United States Patent [19]
Woite et al.

[11] Patent Number: 5,585,917
[45] Date of Patent: Dec. 17, 1996

[54] METHOD AND APPARATUS FOR CHECKING CONTAINERS

[75] Inventors: Rainer Woite, Schwalbach am Taunus; Volker Till, Hofheim am Taunus, both of Germany

[73] Assignee: GEA Till GmbH & Co., Kriftel, Germany

[21] Appl. No.: 404,978

[22] Filed: Mar. 16, 1995

[30] Foreign Application Priority Data

Mar. 16, 1994 [DE] Germany ............................ 44 08 948.1

[51] Int. Cl.⁶ .................................................. G01N 21/00
[52] U.S. Cl. ........................... 356/237; 356/240; 348/127; 382/142
[58] Field of Search ...................................... 356/237, 240, 356/375, 394, 428; 250/223 B, 559.19, 559.2, 559.24, 559.27, 559.3, 559.45; 348/127, 125, 86; 382/141, 142, 143

[56] References Cited

U.S. PATENT DOCUMENTS

| | | | |
|---|---|---|---|
| 4,107,523 | 8/1978 | Corman | 250/223 B |
| 4,165,939 | 8/1979 | Woodrow et al. | 356/237 |
| 4,682,220 | 7/1987 | Beurskens | 250/223 B |
| 4,924,107 | 5/1990 | Tucker . | |
| 5,126,556 | 6/1992 | Domenico et al. | 356/240 |
| 5,233,199 | 8/1993 | Toyama | 250/559.36 |
| 5,369,713 | 11/1994 | Schwartz et al. | 356/240 |
| 5,461,228 | 10/1995 | Kirkman et al. | 356/240 |

FOREIGN PATENT DOCUMENTS

| | | |
|---|---|---|
| 0150846 | 1/1985 | European Pat. Off. . |
| 0426968A1 | 9/1990 | European Pat. Off. . |
| 3623076A1 | 7/1986 | Germany . |

*Primary Examiner*—Hoa Q. Pham
*Attorney, Agent, or Firm*—Chilton, Alix & Van Kirk

[57] ABSTRACT

A method of and apparatus for determining whether kegs, which are to be cleaned and filled on a bottling plant production line, have physical distortions which may prevent cleaning and/or filling and/or emptying. The testing of the barrels is accomplished by capturing images of the ends and processing the data commensurate with the captured images to identify radial distortion. Axial distortion, which may accompany any radial distortion, is determined by measuring the distances between plural points on the keg and a reference plane to which the keg axis would, under normal conditions, be transverse.

23 Claims, 6 Drawing Sheets

METHOD AND APPARATUS FOR CHECKING CONTAINERS

BACKGROUND OF THE INVENTION

1. Field of the Invention

The present invention relates to the checking of containers prior to use and particularly to the automated testing of resuable barrels prior to the filling thereof with a beverage to ensure that the shape of such barrels is within a predetermined tolerance range when compared to a "new" barrel. More specifically, this invention is directed to non-contacting, dimensional testing apparatus for ensuring that returned kegs have not been damaged to such a degree that they cannot be successfully processed on a production line of an automated bottling plant. Accordingly, the general objects of the present invention are to provide novel and improved methods and apparatus of such character.

2. Description of the Prior Art

While not limited thereto in its utility, the present invention is particularly well suited for use in the beverage industry. It is common practice in the beverage industry to employ barrel-like containers to transport a beverage from a bottling plant to the user. Such barrels, when provided with a screw-in fitting having an integral shut-off valve, are commonly referred to as kegs. These kegs are customarily fabricated from stainless steel or a combination of stainless steel and other materials such as, for example, polyurethene or rubber. When materials other than steel are employed, such materials will typically be found in that region of the keg which is subject to mechanical loading during transit, i.e., in the area near the barrel collars or ends. Kegs are returnable containers which are brought back to the bottling plant for cleaning and refilling after being emptied by the customers. Because of their sturdy construction, kegs can customarily be used for a large number of cycles between the bottling plant and the users. As the age of a keg and the number of cycles of its use increases, the possibility of its becoming deformed and damaged also increases. A badly deformed keg will cause a production line interruption in the production line of the bottling plant.

In order to avoid production line interruptions in a bottling plant, and to also avoid the necessity of physically measuring returned containers to ensure that any deformation or other exterior damage thereto is of insufficient magnitude to preclude reuse, a technique for the automated inspection of kegs prior to use has long been desired. Such an automated inspection technique, if available, would be installed upstream of a bottling plant production line and would be used to separate out damaged containers before the start of the cleaning and bottling cycle.

SUMMARY OF THE INVENTION

The present invention overcomes the above-briefly discussed and other deficiencies and disadvantages of the prior art by providing a testing procedure for quantifying the degree of damage to reusable containers, particularly kegs, prior to the insertion thereof onto an automated production line of a bottling plant. The invention also encompasses apparatus for use in the practice of the method and particularly apparatus which employs imaging technology.

In the practice of the invention, a "picture" is taken of the keg being checked, for example the bottom of the keg with its collar, and that "picture" is converted into image data for processing by a computer. The computer performs an evaluation of the image data, the evaluation including a comparison with data commensurate with an acceptable container, and produces a signal indicative of whether the container should be separated out for repair. Use of an image processing system to check barrels permits the testing procedure to be highly automated, i.e., if the image data for the barrel being studied are found to be outside predetermined tolerance ranges, the barrel will be classified as deformed and automatically ejected from the production line.

The most frequent damage to kegs constitutes deformation of the collars, the collars being provided to afford protection to the top and bottom and fitting. Collar damage may, for example, occur when a filled keg is dropped on its collar. In accordance with a preferred embodiment of the invention, the outer and/or inner diameters of the barrel collars at a plurality of evenly spaced locations about the periphery of the barrel are determined from the captured image. This determination allows the detection of radial deformations. Also, since preferably the inner and outer diameters of the collars of each incoming barrel are determined, an automated analysis of the deformation of the barrel collars can be automatically performed regardless of the type of barrel. Thus, the present invention has the attribute of enabling the processing of barrels regardless of diameter without calibration.

In the preferred embodiment being described, the outer and/or inner diameter of the barrel collar is found at eight places on the image. It has been found that the taking of measurements at eight locations which are generally evenly spaced about the barrel periphery permits a sufficiently accurate analysis of the shape of the collar for the purposes of the present invention.

In the practice of the invention, in accordance with one embodiment, a "best outer circle" and "best inner circle" can be determined from the image data commensurate with a barrel collar. These "best circles" can then be used for analyzing deformations of the barrel collar. Specifically, deviations of the actual outer diameter from the "best outer circle" can be determined. Similarly, the actual inner diameter of the barrel collar may be compared with the "best inner circle". The embodiment of the invention wherein the "best circles" are employed allows the invention to be utilized in the testing of a wide variety of barrel types since the "best circle" for each individual barrel is computed and then employed in the deformation analysis.

A particular advantage of the present invention resides in its ability to discriminate between barrels which can be accepted for processing and barrels which either are defective, i.e., too badly deformed for use, or have not been sold by the brewery to which returned. Such discrimination is possible because the best inner and outer diameter of the barrel collar of the keg being tested may be compared with previously stored "best circles" of normal barrels, i.e., barrels with acceptable dimensions, which have been sold by the brewery. Thus, it is possible to separate out "foreign" barrels automatically.

In accordance with yet another embodiment of the invention, the testing procedure includes determining the number of pixels in the collar image which are located outside the "best outer circle" and inside the "best inner circle" which are calculated from the barrel image data. Also, the number of pixels located between the "best circles" is determined. By comparing the pixel numbers, a quantitative analysis of the barrel collar deformation can be made. In the application of this embodiment, since no pixels will be counted from a region of the barrel collar which is crimped axially, a barrel may be rejected when no pixels are detected in a peripheral area of its collar.

A barrel collar can, of course, also be deformed axially by being crooked, i.e., axial deformation will occur if the plane defined by the collar is tiled at an angle other than 90° with respect to the barrel axis. In accordance with the present invention it is also possible, by determining the distance between various peripheral areas of the barrel collar and a reference plane, to identify a general axial deformation, as opposed to an individually crimped portion, of the collar. Such measurements of distance between a reference plane and the collar can expeditiously be accomplished using coherent light or ultrasound. Alternatively, multiple cameras can be employed and the distance detected by stereometric techniques.

Another condition commonly encountered is that the end of a barrel which is positioned for imaging is not deformed but the entire barrel is crushed, i.e., inclined at an angle, because of an axial deformation of the collar on the opposite end thereof. In this situation, an analysis of the image of the collar on the non-deformed side reveals, rather than a circular pattern, a collar image which has an elliptical shape. Also in the case of an opposite end deformation, measurements of collar distance from a reference plane would indicate a collar deformation when no deformation in fact exists. To prevent such erroneous information, the distance between a plurality of reference points on the end of the barrel within the collar and the reference plane will be measured and these distances analyzed to determine which end of the barrel is deformed. Preferably, four reference points, staggered 90° with respect to one another, on the bottom of the barrel are used.

It should be noted that the protection afforded the end of a barrel-like keg by the collar will usually prevent deformation of the end during use. Accordingly, in the above-discussed technique, the keg bottom, at a series of points displaced around the fitting, can be used in calculating whether the barrel is crooked. Thus, in the practice of the invention, the distance from the individual reference points on the bottom of the barrel to the reference plane are related to one another, the relative position of the bottom of the barrel with respect to horizontal is calculated and, if the barrel is found to be crooked, the image of the barrel collar will be corrected as a function of the inclination of the barrel. After such image data adjustment, a determination will be made as to whether the collar of the barrel being checked is actually deformed or an error message resulting from the initial image analysis was attributable to the fact that the barrel was supported so that its axis was inclined with respect to the vertical.

The present invention thus also contemplates the imaging of the top and/or bottom of a barrel to be tested, the evaluation of such image(s) and the rejection of the barrel if the image data for the top and/or bottom lies outside a predetermined tolerance range.

Barrels being processed in a bottling plant are cleaned and filled via the integral valve in the barrel fitting, the fitting being screwed into a bushing in the bottom of the barrel and extending into the barrel generally coaxially with the barrel axis. If the bushing is damaged during transport, the fitting will be misaligned with respect to the barrel axis. A misaligned fitting may prevent adequate cleaning, filling or emptying. Accordingly, in one preferred form of the invention, a determination is also made as to whether the barrel has been damaged such that the fitting is misaligned. This may be accomplished by determining the "vertical" distance between the top of the fitting to the adjacent bottom of the barrel at a plurality of reference points on the surface of the fitting, there being at least two such reference points located at diametrically opposite positions. The barrel will be rejected if the distances between the at least two reference points on the top of the fitting and the bottom of the barrel differ by more than a predetermined amount. As mentioned above, since the bottom of the barrel is usually not deformed, an out of tolerance distance difference between the reference points on the top of the fitting and the bottom of the barrel will indicate a crooked, i.e., misaligned, fitting.

Apparatus in accordance with the invention comprises at least one "camera" for capturing an image of a section of a barrel to be tested. The imaged section of the barrel will be typically be an end including the surrounding collar. The apparatus also includes a data processor in which data commensurate with the captured image is evaluated. The camera may be a CCD line camera or a video camera. The data processor will be provided with a memory for storing the image data and corresponding data for known types of barrels.

Apparatus in accordance with the invention may also include means for determining the distance between individual points on a barrel being tested, particularly points on the collar and/or end and/or fitting, and a reference plane. These distance measurements may then be processed to detect a partially crushed or otherwise damaged collar on the top or bottom of the barrel or a misaligned barrel fitting. The distance measuring devices may employ optical or acoustical techniques.

In accordance with a particularly convenient embodiment of the invention, an image capture device is positioned both upstream and downstream of a barrel turning station whereby images of both the top and bottom of the barrel may be captured. Since a turning machine is usually arranged at the upstream end of a bottling plant production line, the present invention enables the early detection of defective barrels through the expedient of simply adding image capture devices to the existing production apparatus. Also, through the incorporation of data storage devices, the present invention permits the data commensurate with the images from both image capture devices to be simultaneously evaluated.

BRIEF DESCRIPTION OF THE DRAWINGS

The present invention may be better understood and its numerous objects and advantages will become apparent to those skilled in the art by reference to the accompanying drawings wherein like reference numerals refer to like elements in the several figures and in which.

DESCRIPTION OF THE DISCLOSED EMBODIMENTS

Figure 1:
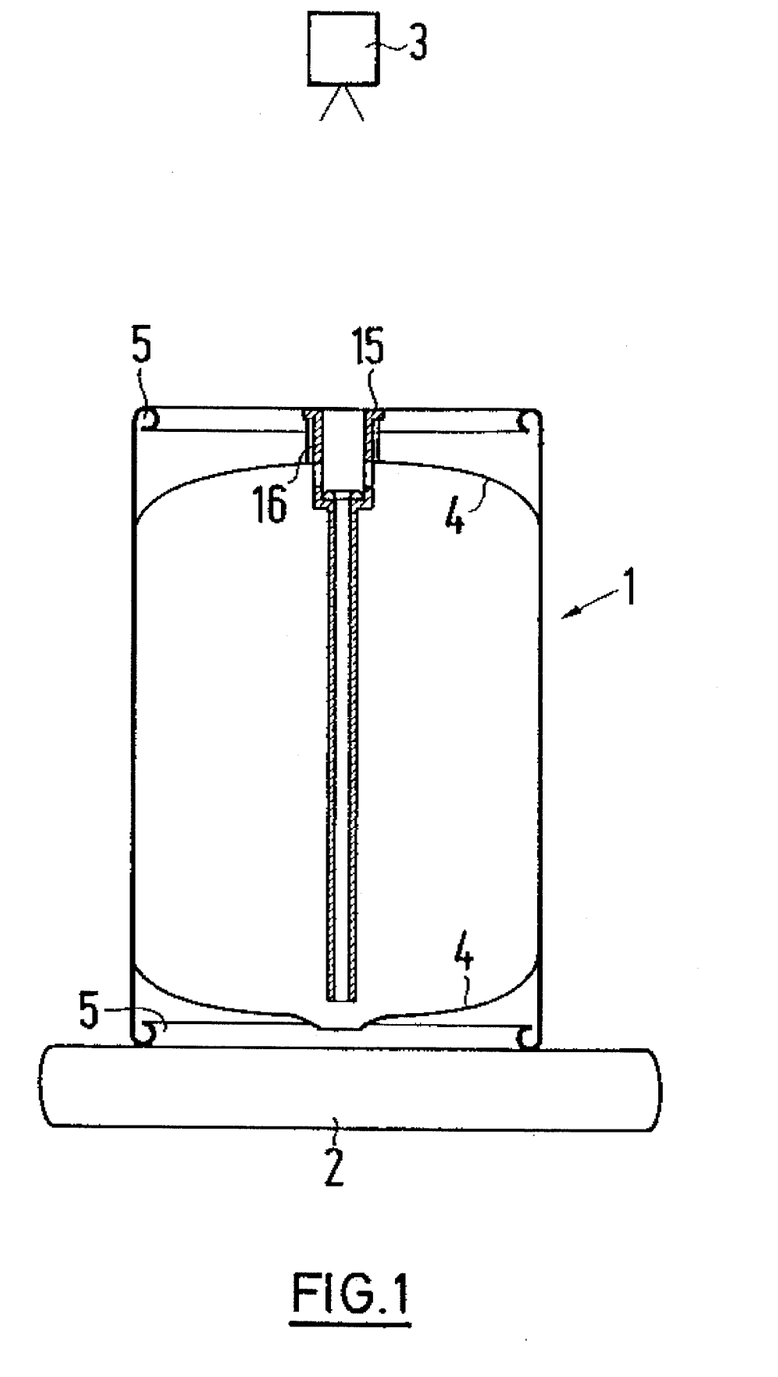
FIG. 1 is a schematic, side-elevation view, partly in section, representing a barrel being tested in accordance with the invention, the barrel being positioned in the field of view of an image capture device.

With reference to FIG. 1, a container of the type which will typically be inspected by employment of the present invention is indicated generally at 1. Container 1 is a reusable barrel, i.e., a keg, which has been returned to the bottling plant for cleaning and refilling after having been emptied by a customer. The present invention comprises methods of and apparatus for the non-destructive, non-contacting dimensional testing of keg 1 for the purpose of ensuring that any deformations thereof which have occurred during use are not sufficiently severe to prevent recyling. Restated, the present invention will check keg 1 to ensure that its size and shape are such that it will not be likely to cause an interruption in a multi-stage cleaning/sterilization and filling process. If a significant deformation is detected, the keg 1 will be separated out of the production flow and sent to a repair station.

Keg 1 includes a pair of ends 4, i.e., a bottom and a top, which are recessed below collars 5. The bottom of keg 1 is provided with a bushing 16. A "fitting" 15, which includes an integral shut-off valve, is threadably received in bushing 16.

At a bottling plant, the barrel 1 is placed on a conveyor 2 which may be considered the most upstream portion of the production line. At an initial stage of its movement along conveyor 2, an image of the bottom 4 of keg 1 will be captured by means of a "camera" 3 which, as noted above, may be a video camera or a CCD device. In the manner well known in the art, for example as used in optical character or pattern recognition, the captured image will be digitized and the resulting data transmitted to a data-processing device, not shown, for evaluation.

Figure 2:
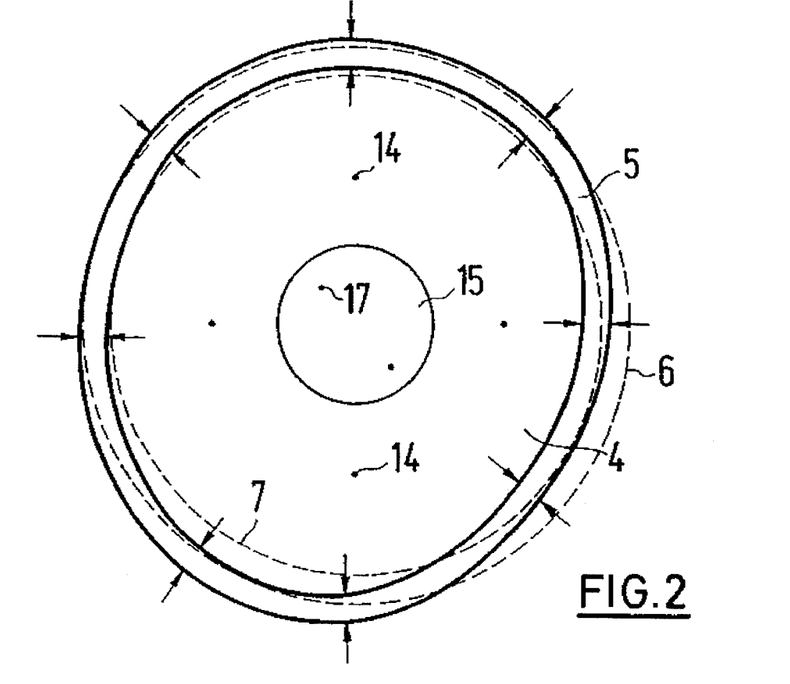
FIG. 2 is a schematic drawing which depicts "best circles" calculated from the image data provided by the apparatus of FIG. 1.

The image captured by camera 3 is depicted schematically in FIG. 2, i.e., FIG. 2 is a representation of a collar 5 which has been deformed irregularly about it periphery and thus deviates from the annular shape characteristic of a new keg. In one embodiment of the invention, the image data is processed to determine the outer and inner diameters of collar 5 at the eight locations indicated by arrows in FIG. 2. The diameter data thus obtained is then processed to compute mean inner and outer diameters and this information is converted into a "best outer circle 6" and a "best inner circle 7". The "best" circles 6 and 7 are represented by broken lines in FIG. 2 and define an annulus. As may be seen from FIG. 2, the actual barrel collar 5 projects outwardly beyond "best" outer circle 6 in some areas and at other places projects inwardly from "best" inner circle 7.

In the embodiment of the invention being described, the maximum and minimum deviations of the outer and inner diameters of collar 5 from the "best" outer and inner circles are determined by comparison. If the determined deviations are outside of a tolerance range, which may have been previously determined by experience, the keg 1 is sufficiently deformed so that proper cleaning or filling cannot be guaranteed. Accordingly, the deformed barrel is ejected from the conveyor and sent to a repair area.

The data processor which performs the above-described computations and comparisons will include a memory which contains the outer and inner diameters of the collars of known kegs. This stored data may be compared with the computed data for the "best" outer circle 6 and the "best" inner circle 7 of the imaged keg 1. If the "best" circle data obtained from the imaged keg 1 deviates by more than a predetermined tolerance range from keg diameter data stored in the memory of the data processor, the keg 1 is a "foreign" keg that does not belong in the bottling plant and/or is not usually sold by the brewery. In such case, the keg 1 will be separated out of the production line.

Figure 3:
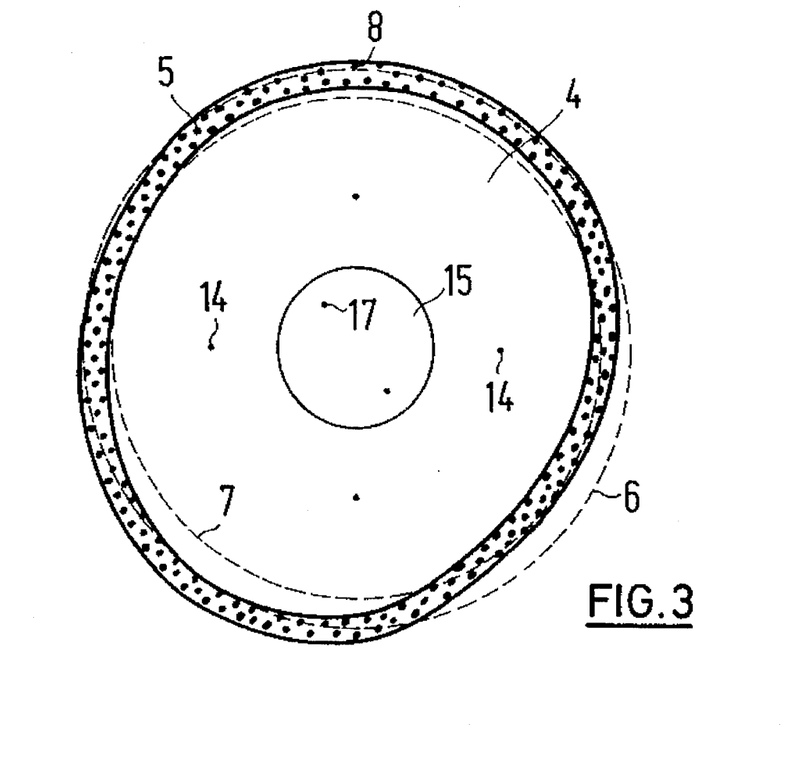
FIG. 3 is a drawing similar to FIG. 2 representing the pixels of an image of the collar of the barrel of FIG. 1.

A modification of the above-described technique is depicted in FIG. 3. In the technique for the qualitative analysis of barrel 1 represented by FIG. 3 the pixels 8 comprising the image of the collar 5 are employed. The analysis encompasses determining the number of pixels which lie outside of the computed "best" outer circle 6 and inside of the "best" inner circle 7 and also the number of pixels of the image which lie in the annulus between the "best" circles. If the ratio of pixels inside and outside of the "best" circles to the number of pixels between the "best" circles falls outside of a predetermined tolerance range, the keg 1 will be rejected and separated out of the production line.

Figure 4:
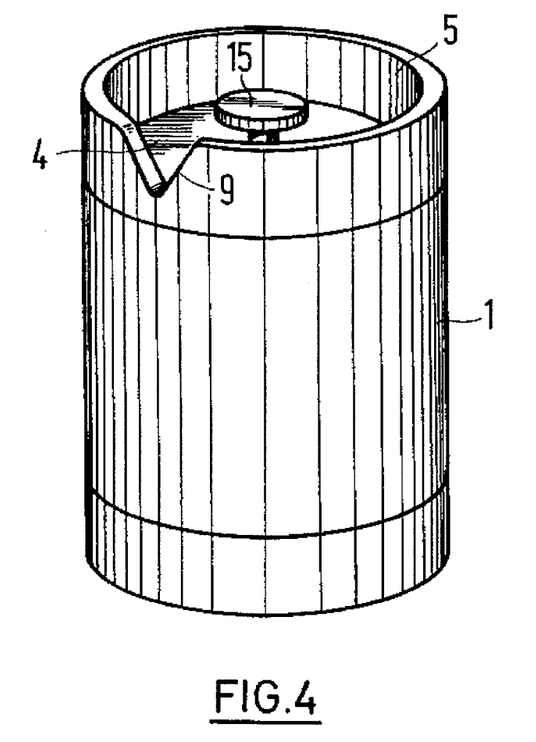
FIG. 4 is a perspective view of a barrel having an axial dent in one of its collars.
Figure 5:
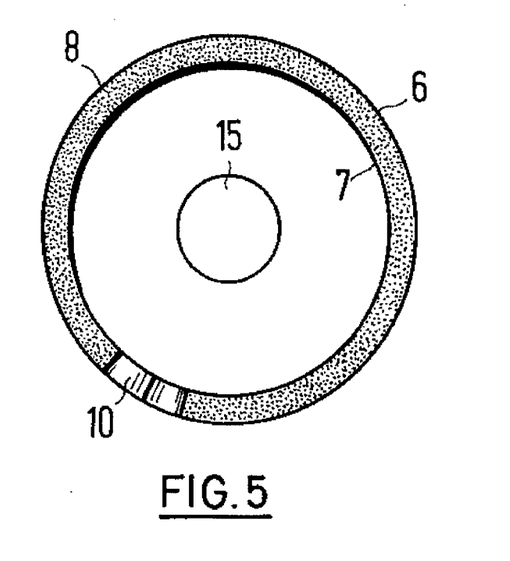
FIG. 5 represents the pixel image of the dented barrel collar of FIG. 4.

The present invention, as described above, determines deformations of the keg collar in the radial direction. However, it is also possible for the collar 5 to be deformed in the axial direction. Such an axially deformed keg 1 is schematically shown in FIG. 4. The keg depicted in FIG. 4 has a axial dent 9 which cannot be found by analyzing the outer and inner diameters of the keg collar 5. However, by analyzing the pixels which comprise the captured image of collar 5, as represented in FIG. 5, it may be seen that there is a gap which corresponds to the area of dent 9, i.e., there will be little or no light reflected to the image capture device from the angled walls of dent 9. Thus, in addition to the analysis of the image data described above in the discussion of FIGS. 2 and 3, the image may also be analyzed to see if there are any abnormalities in the image which are commensurate with an axial collar deformation and, if so, the keg will be ejected.

Figure 6:
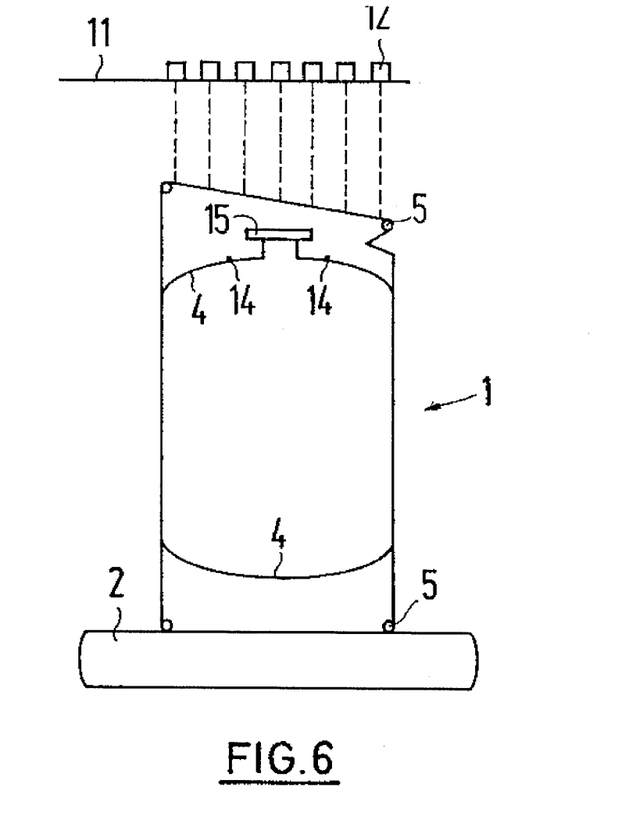
FIG. 6 schematically illustrates the measurement of the distance between the collar of a test barrel and a reference plane.
Figure 7:
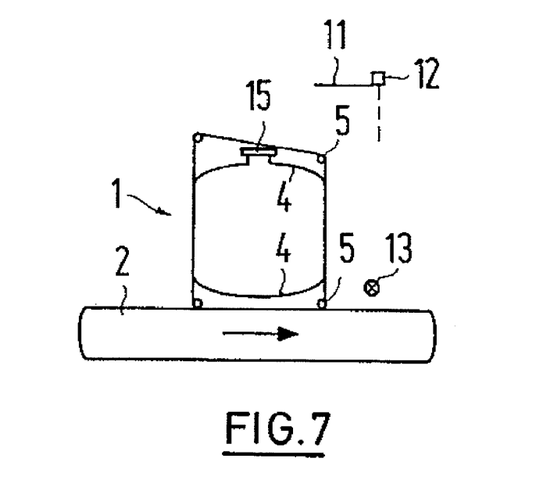
FIG. 7 is another view of the distance measuring installation shown in FIG. 6.

FIGS. 6 and 7 schematically represent a condition wherein the collar 5 about the keg bottom has been crimped at one side thus resulting in the plane defined by the top of the collar being skewed with respect to horizontal. The type of deformation depicted in FIGS. 6 and 7 can be identified by measuring the distance from the collar 5 to a horizontal reference plane 11. Such distance measuring may be performed by means of an array of sensors 12 which are positioned over the conveyor 2. The sensors 12 can be conventional optical range measuring devices, for example devices which employ coherent light, or acoustical, and particularly ultrasound, distance measuring instruments. As an alternative, which has not been shown, the distance can be determined by employing two cameras and utilizing the technique known as stereometry. Since the sensors 12 are highly focused, a comparatively large number of such devices arranged diagonally with respect to belt 2 will be utilized. The beginning of the distance measurement procedure will be triggered by means of a photocell 13 (see FIG. 7). The sensors 12 will store the measured values and transmit signals commensurate therewith to the data processor. If the test procedure indicates that the barrel collar 5 is crooked, i.e., defines a plane which is badly skewed with respect to the reference plane, the keg 1 will be ejected.

Figure 8:
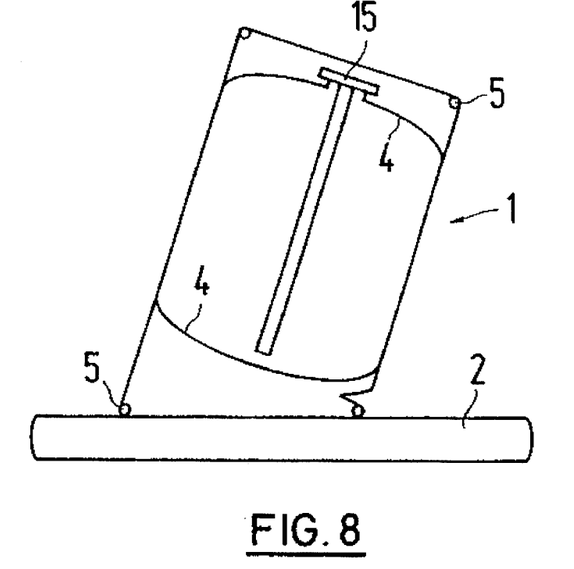
FIG. 8 is a schematic front elevational view of a crooked barrel.

A skewed barrel collar defined plane may, as shown in FIG. 8, also result from the collar at the top of the barrel being crimped rather than the bottom collar as represented in FIGS. 6 and 7. If the condition represented by FIG. 8 is encountered, the information derived from the distance data provided by the array of sensors 12 and the information derived from the image data analysis represented by FIGS. 2 and 3 may incorrectly indicate an "error", i.e., a need to eject the barrel. Restated, the sensors 12 will provide signals indicating that the collar 5 is not horizontal. At the same time, the analysis of the captured image of the collar 5 about the bottom of the keg, employing the technique represented by either FIG. 2 or FIG. 3, will reveal an elliptical collar which does not coincide with the "best" circles 6, 7 which have been computed. To guard against false "error" signals, the distance between reference plane 11 and four reference points 14 (see FIGS. 2 and 3), staggered 90° with respect to one another, on the bottom 4 of keg 1 will be determined. Since the bottom 4 of keg 1 is protected by the collar 5, with a "normal" keg 1 it can be assumed that a plane defined by plural points on the keg bottom will be parallel to the reference plane. Thus, if the distance measured between reference points 14 and reference plane 11 indicates that the plane defined by points 14 is inclined with respect to the horizontal, it must be concluded that the collar 5 at the top of keg 1 has been seriously deformed. The angle of inclination of the plane defined by reference points 14 can be computed from the measured distances by the data processor and this inclination angle employed as a correction factor for the information obtained by the sensors 12 and the information used in plotting the "best circles" 6, 7. A crimped top collar, as represented in FIG. 8, may not preclude use of the keg. As should be obvious, the shape of the collar at the bottom of the keg is evaluated relative to the "best circles" 6, 7 only after compensation for the angle of inclination of the collar at the opposite end.

Figure 9:
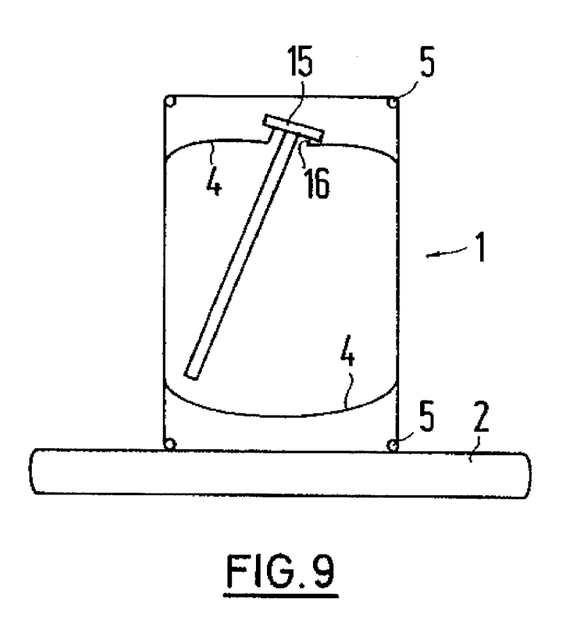
FIG. 9 is a schematic front elevational view of a barrel having a crooked fitting.

The keg 1 is cleaned and filled through fitting 15. It is possible, during transportation, that the bushing 16 in the keg bottom 4 which receives the fitting 15 will become deformed. The fitting 15 is normally arranged so as to be generally coaxial with keg 1. If bushing 16 is deformed, fitting 15 may be forced out of its normal coaxial relationship to keg 1 as represented in FIG. 9. Such a misaligned fitting 15 may be detected by distance measurements taken from at least a pair of reference points 17 (see FIGS. 2 and 3) on the top of the fitting. Thus, using sensors as described above with respect to FIG. 6, the distances between the reference plane and points 17 on the fitting and the points 14 on the keg bottom will be determined and the displacements of the points 17 from the plane of the keg bottom will then be calculated. If it is determined that there is a difference in the distance between the oppositely disposed test points 17 on fitting 15 and the plane defined by the points 14 on the keg bottom, the fitting will be considered to be misaligned and the keg rejected.

Figure 10:
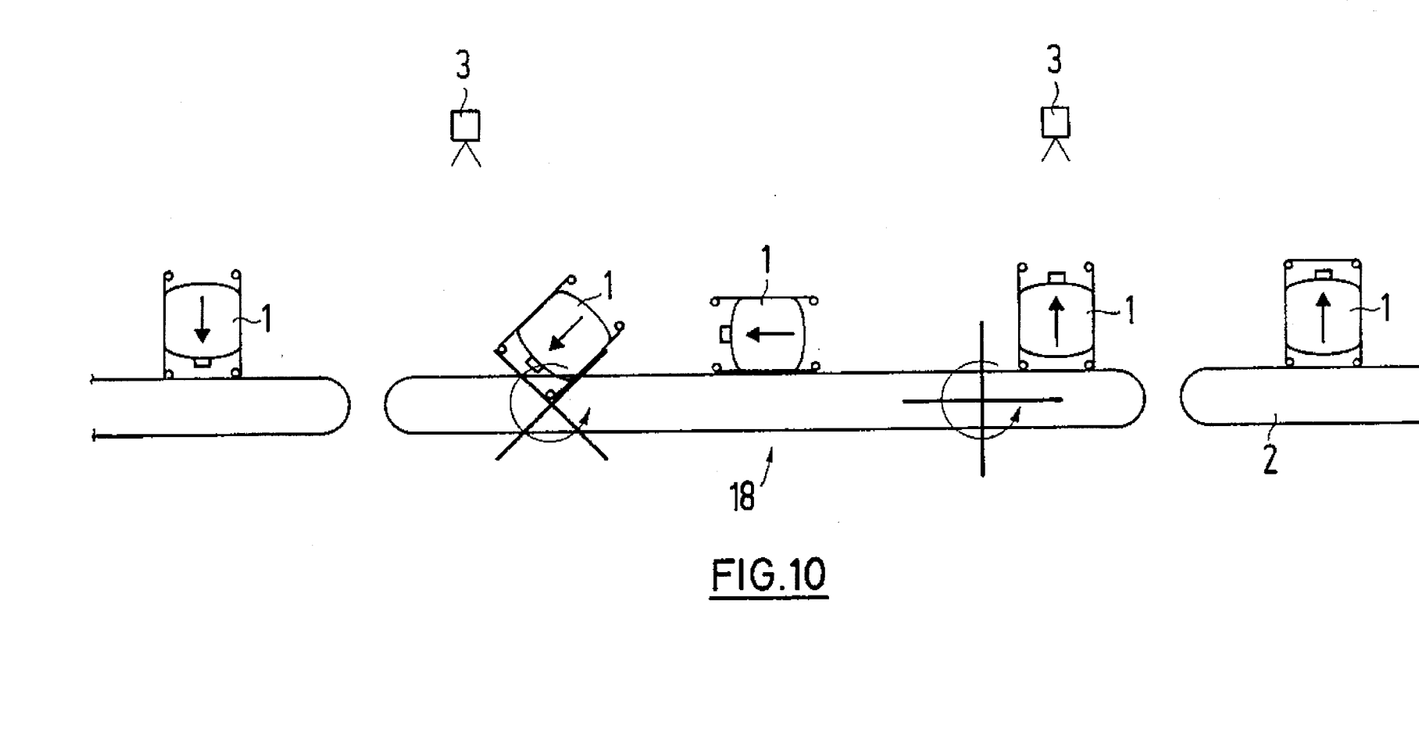
FIG. 10 schematically illustrates the installation of the present invention at the turning station of a bottling plant production line.

With the exception of the checking of the fitting 15, the above-described evaluation should preferably be performed with respect to both the bottom and top of keg 1. Accordingly, as shown in FIG. 10, an installation in accordance with the invention preferably employs image capture devices 3 arranged both upstream and downstream of a turning station 18 of a bottling plant production line. Such turning stations are already present in bottling plants since the kegs 1 are customarily delivered to the plants on pallets with the fitting 15 facing upwardly. The kegs 1 are usually placed on conveyor 2 in the orientation in which delivered, i.e., with the fitting 15 up. However, the cleaning and/or filling cycle is usually carried out with the fitting 15 facing downwardly. Thus, a bottling plant production line will be provided with a turning station which engages and inverts the incoming kegs. As shown in FIG. 10, the present invention contemplates the positioning of a first image capture device 3 upstream of the point where the inverting of the incoming keg occurs and a second image capture device 3 downstream of where the turning has been completed. The image data provided by the image capure devices 3 will be evaluated together. If such evaluation reveals serious deformation of the collar 5 on either end of the keg, or if the distance measurements obtained by the sensors 12 (which have not been shown in FIG. 10) show dmage in the area of the fitting 15 on the keg bottom, an error message will be generated by the associated data processor, the error will be reported to the plant controller and the keg 1 will be ejected immediately downstream of the turning station 18. Obviously, only a single ejector located downstream of the turning station is required. The arrangement of FIG. 10 ensures that, before the bottling process starts, all badly deformed kegs are separated out of the incoming stream of kegs so that they will not cause a jam or other problem in the cleaning and filling steps which are performed downstream of the turning station.

The image capture devices 3 can be used for checking other properties of the incoming kegs in addition to those discussed above. By way of example, analysis of an image provided by a camera 3 can provide information as to whether the keg has a label containing information such as, for example, the minimum perishability date for the beverage in the keg. If such a label is missing, the keg will be ejected. Obviously, any other information that is optically detectable can be ascertained employing the above-described techniques. It may, for example, be possible to detect leakage of the fitting 15 through image analysis.

While preferred embodiments have been shown and described, various modification and substitutions may be made thereto without departing from the spirit and scope of the invention. Accordingly, it is to be understood that the present invention has been described by way of illustration and not limitation.

What is claimed is:

1. A process for the pre-processing testing of generally barrel-shaped containers for deformation, each container having a pair of oppositely disposed ends and a collar which extends about at least one of said container ends, said process comprising the steps of:

capturing an image of at least the said one container end and the adjacent collar;

processing the image to determine the inner and outer diameters of the collar at a plurality of locations spaced about the periphery of the container;

employing the determined diameters to analyze the degree of distortion of the collar, said step of employing the determined diameters including:

calculating mean inner and outer collar diameters from the determined inner and outer diameters respectively;

comparing the calculated mean inner and outer diameters with the determined inner and outer diameters respectively;

determining deviations between the determined outer diameters and a circle defined by the calculated mean outer diameter; and determining deviations between the determined inner diameters and a circle defined by the calculated mean inner diameter.

2. The method of claim 1 wherein the diameters of the collar are determined at eight positions substantially evenly displaced about the container periphery.

3. The process of claim 1 wherein said step of comparing comprises determining deviations between the maximum and minimum inner and outer determined diameters and the circles defined by the calculated mean inner and outer diameters respectively.

4. The process of claim 1 further comprising:

storing information commensurate with the calculated mean inner and outer diameters of a plurality of normal containers; and comparing the calculated mean inner and outer diameters with the stored mean diameter information to determine if the container should be processed.

5. The process of claim 1 wherein the container is provided with collars which extend about both container ends, and wherein said process further comprises the steps of:

capturing the image of the other container end and the adjacent collar;

processing the image of the other container end and the adjacent collar to determine the inner and outer diameters of the collar at a plurality of locations spaced about the periphery of the other container end; and employing the determined diameters of the collar at the other container end to analyze the degree of distortion of the collar at the other container end.

6. The process of claim 1 wherein the container has an axis and is provided with a fitting supported in the said one end thereof, the fitting extending into the container, and wherein said process further comprises:

measuring the displacement in the axial direction of the container between at least a pair of points on the fitting and a pair of reference points on the said one container end;

comparing the measured displacements; and generating an error signal if the comparison indicates that one of the measured displacements varies from the other by more than a predetermined amount.

7. A process for the pre-processing testing of generally barrel-shaped containers for deformation, each container having a pair of oppositely disposed ends and a collar which extends about at least one of said container ends, said process comprising the steps of:

capturing an image of at least the said one container end and the adjacent collar;

processing the image to determine the inner and outer diameters of the collar at a plurality of locations spaced about the periphery of the container;

employing the determined diameters to analyze the degree of distortion of the collar;

measuring the distance between a reference plane and a plurality of points on the container collar; and comparing the measured distances to determine if a plane defined by the collar is angularly inclined with respect to the reference plane.

8. The process of claim 7 further comprising:

measuring the distance between a reference plane and a plurality of measuring points on the end of the container disposed within the collar; and comparing the measured distances between the reference plane and container end to determine if a plane defined by the measuring points on the container end is inclined at an angle with respect to the reference plane.

9. The process of claim 8 wherein the container has an axis and is provided with a fitting supported in the said one end thereof, the fitting extending into the container, and wherein said process further comprises:

measuring the displacement in the axial direction of the container between at least a pair of points on the fitting and a pair of reference points on the said one container end;

comparing the measured displacements; and generating an error signal if the comparison indicates that one of the measured displacements varies from the other by more than a predetermined amount.

10. The method of claim 9 wherein an angularly inclined container bottom is construed as a dimensional distortion at the opposite end of the container and wherein said method further comprises:

determining the angle of inclination of the container bottom and using the determined inclination angle as a correction factor during the processing of the captured image to determine the inner and outer collar diameters.

11. The process of claim 9 wherein the step of calculating provides the mean inner and outer collar diameters and the step of comparing comprises determining deviations between the maximum and minimum outer and inner diameters of the actual collar and the circles defined by the calculated mean inner and outer diameters.

12. The process of claim 11 wherein the container is provided with collars which extend about both ends thereof, and wherein said process further comprises the steps of:

capturing an image of the other container end and the adjacent collar;

processing the image of the other container end and collar to determine the inner and outer diameter of the collar at a plurality of locations spaced about the periphery of the container other end; and employing the determined diameters of the collar at the other container end to analyze the degree of distortion of the collar at the container other end.

13. The method of claim 12 wherein an angularly inclined container bottom is construed as a dimensional distortion at the opposite end of the container and wherein said method further comprises:

determining the angle of inclination of the container bottom and using the determined inclination angle is a correction factor during the processing of the captured image to determine the inner and outer collar diameters.

14. A process for the pre-processing testing of generally barrel-shaped containers for deformation, each container having a pair of oppositely disposed ends and a collar which extends about at least one of said container ends, said process comprising the steps of:

capturing an image of at least the said one container end and the adjacent collar;

processing the image to determine the inner and outer diameters of the collar at a plurality of locations spaced about the periphery of the container;

employing the determined diameters to analyze the degree of distortion of the collar;

measuring the distance between a reference plane and a plurality of measuring points on the end of the container disposed within the adjacent collar; and comparing the measured distances between the reference plane and container end to determine if a plane defined by the measuring points on the container end is angularly inclined with respect to the reference plane.

15. The method of claim 14 wherein an angularly inclined container bottom is construed as a dimensional distortion at the opposite end of the container and wherein said method further comprises:

determining the angle of inclination of the container bottom; and using the determined inclination angle as a correction factor during the processing of the captured image to determine the inner and outer collar diameters.

16. The process of claim 15 wherein the step of employing the determined diameters to analyze the degree of distortion comprises:

calculating the mean inner and outer collar diameters from the determined inner and outer diameters respectively;

counting the number of pixels comprising the captured image which lie within an annulus defined by the calculated mean inner and outer diameters;

counting the number of pixels comprising the captured image which lie outside of the annulus defined by the calculated mean inner and outer diameters; and comparing the number of pixels lying within and outside the annulus.

17. The process of claim 16 wherein the container is provided with collars which extend about both ends thereof, and wherein said process further comprises the steps of:

capturing an image of the other container end and the adjacent collar;

processing the image of the other container end and collar to determine the inner and outer diameter of the collar at a plurality of locations spaced about the periphery of the container other end; and employing the determined diameters of the collar at the other container end to analyze the degree of distortion of the collar at the container other end.

18. The method of claim 17 wherein an angularly inclined container bottom is construed as a dimensional distortion at the opposite end of the container and wherein said method further comprises:

determining the angle of inclination of the container bottom and using the determined inclination angle as a correction factor during the processing of the captured image to determine the inner and outer collar diameters.

19. Apparatus for use in the pre-processing testing of generally barrel-shaped containers for deformation, the containers having a pair of oppositely disposed ends and collars which extend about said ends, said apparatus comprising:

at least a first image capture device for capturing an image of a section of the container to be tested, the captured section including the bottom of the container with the surrounding collar;

means for processing the captured image; and means for measuring the distance between a plurality of points on the container section which is imaged and a reference plane.

20. The apparatus of claim 19 wherein the container is moved along a transport path and said first image capture device is positioned on a first side of the transport path at a location upstream of an apparatus for turning the container through an angle of 180°, and wherein said apparatus further comprises:

a second image capture device located downstream of the turning apparatus and on the same side of the transport path as said first image capture device whereby images of the opposite ends of the container are captured.

21. A process for the pre-processing testing of generally barrel-shaped containers for deformation, each container having a pair of oppositely disposed ends and a collar which extends about at least one of said container ends, said process comprising the steps of:

capturing an image of at least the said one container end and the adjacent collar;

processing the image to determine the inner and outer diameters of the collar at a plurality of locations spaced about the periphery of the container;

employing the determined diameters to analyze the degree of distortion of the collar, said step of employing the determined diameters including:

calculating the mean inner and outer collar diameters from the determined inner and outer diameters respectively;

counting the number of pixels comprising the captured image which lie within an annulus defined by the calculated mean inner and outer diameters;

counting the number of pixels comprising the captured image which lie outside of the annulus defined by the calculated mean inner and outer diameters; and comparing the number of pixels lying within and outside the annulus.

22. The process of claim 21 further comprising:

generating a container reject signal if no pixels can be counted in a peripheral area of the captured image of the collar.

23. A process for the pre-processing testing of generally barrel-shaped containers for deformation, each container defining an axis and having a pair of oppositely disposed ends, a collar which extends about at least one of said container ends, and a fitting which is supported by, and extends into, the said one container end, said process comprising the steps of:

capturing a image of at least the said one container end and the adjacent collar;

processing the image to determine the inner and outer diameters of the collar at a plurality of locations spaced about the periphery of the container;

employing the determined diameters to analyze the degree of distortion of the collar;

measuring the displacement in the axial direction of the container between at least a pair of points on the fitting and a pair of reference points on the said one container end;

comparing the measured displacements; and generating an error signal if the comparison indicates that at least one of the measured displacements varies from the other by more than a predetermined amount.

* * * * *